(12) United States Patent
Pettis et al.

(10) Patent No.: US 8,986,280 B2
(45) Date of Patent: *Mar. 24, 2015

(54) INTRADERMAL DELIVERY OF SUBSTANCES

(71) Applicant: Becton, Dickinson and Company, Franklin Lakes, NJ (US)

(72) Inventors: Ronald J. Pettis, Cary, NC (US); James A. Down, Randolph, NJ (US); Noel G. Harvey, Efland, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/866,425

(22) Filed: Apr. 19, 2013

(65) Prior Publication Data

US 2013/0237960 A1  Sep. 12, 2013

Related U.S. Application Data

(62) Division of application No. 09/606,909, filed on Jun. 29, 2000, now Pat. No. 8,465,468.

(51) Int. Cl.
*A61M 31/00* (2006.01)
*A61M 5/158* (2006.01)
(Continued)

(52) U.S. Cl.
CPC ................. *A61M 5/158* (2013.01); *A61M 5/32* (2013.01); *A61M 5/3286* (2013.01);
(Continued)

(58) Field of Classification Search
CPC ................. A61M 2037/0061; A61M 37/0015; A61M 2037/0023; A61K 38/28; A61K 9/0021
USPC ................... 604/117, 21, 272–274, 500–522, 604/890.1–892.1
See application file for complete search history.

(56) References Cited

U.S. PATENT DOCUMENTS 2,619,962 A  12/1952 Rosenthal
3,814,097 A  6/1974 Granderton et al.
(Continued)

FOREIGN PATENT DOCUMENTS

CA  2349431  5/2000
EP  0692270  1/1996
(Continued)

OTHER PUBLICATIONS

U.S. Appl. No. 14/215,271, filed Mar. 17, 2014, Pettis et al.
(Continued)

*Primary Examiner* — Kevin C Sirmons
*Assistant Examiner* — Phillip Gray
(74) *Attorney, Agent, or Firm* — Jones Day (57) ABSTRACT

The present invention provides improved methods for ID delivery of drugs and other substances to humans or animals. The methods employ small gauge needles, especially microneedles, placed in the intradermal space to deliver the substance to the intradermal space as a bolus or by infusion. It has been discovered that the placement of the needle outlet within the skin and the exposed height of the needle outlet are critical for efficacious delivery of active substances via small gauge needles to prevent leakage of the substance out of the skin and to improve absorption within the intradermal space. The pharmacokinetics of hormone drugs delivered according to the methods of the invention have been found to be very similar to the pharmacokinetics of conventional SC delivery, indicating that ID administration according to the methods of the invention is likely to produce a similar clinical result (i.e., similar efficacy) with the advantage of reduction or elimination of pain for the patient. Delivery devices which place the needle outlet at an appropriate depth in the intradermal space and control the volume and rate of fluid delivery provide accurate delivery of the substance to the desired location without leakage.

10 Claims, 5 Drawing Sheets

(51) Int. Cl.
  *A61M 5/32* (2006.01)
  *A61M 5/46* (2006.01)
  *A61M 37/00* (2006.01)

(52) U.S. Cl.
  CPC .............. *A61M 5/3291* (2013.01); *A61M 5/46* (2013.01); *A61M 37/0015* (2013.01); *A61M 2037/0038* (2013.01); *A61M 2037/0061* (2013.01)
  USPC .......................................... 604/503; 604/117

(56) References Cited

U.S. PATENT DOCUMENTS

| | | | |
|---|---|---|---|
| 3,964,482 A | 6/1976 | Gerstel et al. |
| 4,270,537 A | 6/1981 | Romaine |
| 4,440,207 A | 4/1984 | Genatempo et al. |
| 4,512,767 A | 4/1985 | Denance |
| 4,592,753 A | 6/1986 | Panoz |
| 4,655,762 A | 4/1987 | Rogers |
| 4,886,499 A | 12/1989 | Cirelli et al. |
| 5,003,987 A | 4/1991 | Grinwald |
| 5,098,389 A | 3/1992 | Cappucci |
| 5,156,591 A | 10/1992 | Gross et al. |
| 5,242,425 A | 9/1993 | White et al. |
| 5,250,023 A | 10/1993 | Lee et al. |
| 5,279,544 A | 1/1994 | Gross et al. |
| 5,279,552 A | 1/1994 | Magnet |
| 5,340,359 A | 8/1994 | Segura Badia |
| 5,417,662 A | 5/1995 | Hjertman et al. |
| 5,484,417 A | 1/1996 | Waitz et al. |
| 5,505,694 A | 4/1996 | Hubbard et al. |
| 5,527,288 A | 6/1996 | Gross et al. |
| 5,536,258 A | 7/1996 | Folden |
| 5,567,495 A | 10/1996 | Modak et al. |
| 5,582,591 A | 12/1996 | Cheikh |
| 5,591,139 A | 1/1997 | Lin et al. |
| 5,741,224 A | 4/1998 | Milder et al. |
| 5,792,120 A | 8/1998 | Menyhay |
| 5,800,420 A | 9/1998 | Gross et al. |
| 5,801,057 A | 9/1998 | Smart et al. |
| 5,807,375 A | 9/1998 | Gross et al. |
| 5,820,622 A | 10/1998 | Gross et al. |
| 5,848,990 A | 12/1998 | Cirelli et al. |
| 5,848,991 A | 12/1998 | Gross et al. |
| 5,876,582 A | 3/1999 | Frazier |
| 5,879,326 A | 3/1999 | Godshall et al. |
| 5,925,739 A | 7/1999 | Spira et al. |
| 5,928,207 A | 7/1999 | Pisano et al. |
| 5,957,895 A | 9/1999 | Sage et al. |
| 5,997,501 A | 12/1999 | Gross et al. |
| 6,007,821 A | 12/1999 | Srivastava et al. |
| 6,056,176 A | 5/2000 | Aftanas et al. |
| 6,056,716 A | 5/2000 | D'Antonio et al. |
| 6,099,504 A | 8/2000 | Gross et al. |
| 6,200,291 B1 | 3/2001 | Di Pietro |
| 6,256,533 B1 | 7/2001 | Yuzhakov et al. |
| 6,319,224 B1 | 11/2001 | Stout et al. |
| 6,334,856 B1 | 1/2002 | Allen et al. |
| 6,346,095 B1 | 2/2002 | Gross et al. |
| 6,482,176 B1 | 11/2002 | Wich |
| 6,494,865 B1 | 12/2002 | Alchas |
| 6,537,242 B1 | 3/2003 | Palmer |
| 6,569,143 B2 | 5/2003 | Alchas et al. |
| 6,591,133 B1 | 7/2003 | Joshi |
| 6,607,513 B1 | 8/2003 | Down et al. |
| 6,611,707 B1* | 8/2003 | Prausnitz et al. .............. 604/21 |
| 6,623,457 B1 | 9/2003 | Rosenberg |
| 6,679,870 B1 | 1/2004 | Finch et al. |
| 6,743,211 B1 | 6/2004 | Prausnitz et al. |
| 6,808,506 B2 | 10/2004 | Lastovich et al. |
| 7,722,595 B2 | 5/2010 | Pettis et al. |
| 8,465,468 B1 | 6/2013 | Pettis et al. |
| 8,708,994 B2 | 4/2014 | Pettis et al. |
| 2001/0056263 A1 | 12/2001 | Alchas et al. |
| 2002/0038111 A1 | 3/2002 | Alchas et al. |
| 2002/0095134 A1 | 7/2002 | Pettis et al. |
| 2002/0156453 A1 | 10/2002 | Pettis et al. |
| 2003/0073609 A1 | 4/2003 | Pinkerton |
| 2003/0093032 A1 | 5/2003 | Py et al. |
| 2003/0100885 A1 | 5/2003 | Pettis et al. |
| 2004/0028707 A1 | 2/2004 | Pinkerton |
| 2004/0073160 A1 | 4/2004 | Pinkerton |
| 2004/0082934 A1 | 4/2004 | Pettis et al. |
| 2004/0170654 A1 | 9/2004 | Pinkerton |
| 2004/0175360 A1 | 9/2004 | Pettis et al. |
| 2004/0175401 A1 | 9/2004 | Pinkerton |
| 2005/0008683 A1 | 1/2005 | Mikszta et al. |
| 2005/0010193 A1 | 1/2005 | Laurent et al. |
| 2005/0096330 A1 | 5/2005 | Boettcher et al. |
| 2005/0096331 A1 | 5/2005 | Das et al. |
| 2005/0096332 A1 | 5/2005 | Jung et al. |
| 2005/0096630 A1 | 5/2005 | Pettis et al. |
| 2005/0096631 A1 | 5/2005 | Pettis et al. |
| 2005/0096632 A1 | 5/2005 | Pettis et al. |
| 2005/0124967 A1 | 6/2005 | Kaestner et al. |
| 2005/0147525 A1 | 7/2005 | Bousquet |
| 2005/0181033 A1 | 8/2005 | Dekker, III et al. |
| 2005/0196380 A1 | 9/2005 | Mikszta et al. |
| 2005/0245594 A1 | 11/2005 | Sutter et al. |
| 2005/0256182 A1 | 11/2005 | Sutter et al. |
| 2005/0256499 A1 | 11/2005 | Pettis et al. |
| 2008/0118465 A1 | 5/2008 | Pettis et al. |
| 2008/0118507 A1 | 5/2008 | Pettis et al. |
| 2008/0119392 A1 | 5/2008 | Pettis et al. |
| 2008/0138286 A1 | 6/2008 | Pettis et al. |
| 2008/0140050 A1 | 6/2008 | Pettis et al. |
| 2008/0147042 A1 | 6/2008 | Pettis et al. |
| 2008/0234656 A1 | 9/2008 | Pettis et al. |
| 2009/0124997 A1 | 5/2009 | Pettis et al. |
| 2011/0190725 A1 | 8/2011 | Pettis et al. |
| 2013/0237960 A1 | 9/2013 | Pettis et al. |
| 2013/0237961 A1 | 9/2013 | Pettis et al. |
| 2013/0245601 A1 | 9/2013 | Pettis et al. |

FOREIGN PATENT DOCUMENTS

| | | |
|---|---|---|
| EP | 0429842 B1 | 8/1996 |
| EP | 1086718 A1 | 3/2001 |
| EP | 1086719 A1 | 3/2001 |
| EP | 1088642 A1 | 4/2001 |
| EP | 1092444 A1 | 4/2001 |
| EP | 1246668 B1 | 10/2002 |
| EP | 1296740 B1 | 11/2007 |
| JP | A 113862 | 3/1999 |
| WO | WO 87/00441 A1 | 1/1987 |
| WO | WO 93/17754 A1 | 9/1993 |
| WO | WO 94/23777 A1 | 10/1994 |
| WO | WO 96/17648 A1 | 6/1996 |
| WO | WO 96/37155 A1 | 11/1996 |
| WO | WO 96/37256 A1 | 11/1996 |
| WO | WO 97/21457 A1 | 6/1997 |
| WO | WO 99/43350 A1 | 9/1999 |
| WO | WO 99/64580 A1 | 12/1999 |
| WO | WO 00/09186 A2 | 2/2000 |
| WO | WO 00/16833 A1 | 3/2000 |
| WO | WO 00/67647 A1 | 11/2000 |
| WO | WO 00/74763 A2 | 12/2000 |
| WO | WO 01/39772 A1 | 6/2001 |
| WO | WO 02/02178 A1 | 1/2002 |
| WO | WO 02/02179 A1 | 1/2002 |
| WO | WO 02/11669 A2 | 2/2002 |
| WO | WO 02/083231 A1 | 10/2002 |
| WO | WO 02/083232 A1 | 10/2002 |
| WO | WO 03/002175 A2 | 1/2003 |
| WO | WO 03/015787 A1 | 2/2003 |
| WO | WO 03/057143 A2 | 7/2003 |
| WO | WO 2004/098676 A2 | 11/2004 |
| WO | WO 2004/101023 A2 | 11/2004 |
| WO | WO 2005/086773 A2 | 9/2005 |
| WO | WO 2005/115360 A2 | 12/2005 |

OTHER PUBLICATIONS

Agrawal et al., 1991, "Pharmacokinetics, Biodistribution, and Stability of Oligodeoxynucleotide Phosphorothioates in Mice," Proc. Natl. Acad. Sci. USA 88:7595-7599.

(56) References Cited

OTHER PUBLICATIONS

Anon, 2004, "Flu vaccine: skin injection method effective in younger people," American Health Line: Research Notes (Nov. 4, 2004).
Autret et al., 1989, "Comparison of Pharmacokinetics and tolerance of Calcitonine administered by Intradermal or Subcutaneous Route," Fundamental Clinical Pharmacology 3(2):170-171.
Autret et al., 1991, "Comparaison des concentrations plasmatiques et de la tolerance d'une dose unique de calcitonine humaine administree par voie intradermique et sous-cutanee," Therapie 46:5-8 (with English Translation).
Ba Wu et al., 1989, "Pharmacokinetics of Methoxyflurane after its Intra-Dermal Inection as Lecithin-Coated Microdroplets," Journal of Controlled Release 9:1-12.
Bader, 1980, "Influenza vaccine experience in Seattle," Am. J. Public Health 70(5):545.
Belshe et al., 2004, "Serum antibody responses after intradermal vaccination against influenza," New England Journal of Medicine 351(22):2286-2294.
Benoni et al., 1984, "Distribution of Ceftazidime in Ascitic Fluid", Antimicrobial Agents and Chemotherapy 25(6):760-763.
Bickers et al., editors, 1984, "Clinical Pharmacology of Skin Disease", Churchill Livingstone, Inc.:57-90.
Bocci et al., 1986, "The Lymphatic Route. IV. Pharmacokinetics of Human Recombinant Interferon α2 and Natural Interferon β Administered Intradermally in Rabbits", International Journal of Phamaceutics 32:103-110.
Branswell, 2004, "Vaccine stretching may be an option for future shortages, pandemics: studies," Canadian Press News Wire (Nov. 3, 2004).
Bresolle et al., 1993, "A Weibull Distribution Model for Intradermal Administration of Ceftazidime", Journal of Pharmaceutical Sciences 82(11):1175-1178.
Bronaugh et al., 1982, "Methods for in Vitro Percutaneous Absorption Studies II. Animal Models for Human Skin," Toxicol. and Applied Pharmacol. 62(3):481-488.
Brooks et al., 1977, "Intradermal administration of bivalent and monovalent influenza vaccines," Ann. Allergy 39(2):110-112.
Brown et al., 1977, "The immunizing effect of influenza A/New Jersey/76 (Hsw1N1) virus vaccine administered intradermally and intramuscularly to adults," J. Infect. Dis. 136 Suppl:S466-71.
Burkoth et al., 1999, "Transdermal and Transmucosal Powered Drug Delivery," Critical Review in Therapeutic Drug Carrier Systems 16(4):331-384.
Callen, 1981, "Intralesional Corticosteriods", Journal of the American Academy of Dermatology, University of Louisville School of Medicine, 149-151.
Communication of a Notice of Opposition to EP 1296740 (Aug. 14, 2008) and Opposition Brief in its entirety.
Communication of a Notice of Opposition to EP 1296740 (Jul. 18, 2008) and Opposition Brief in its entirety.
Corbo et al., 1989, "Transdermal Controlled Delivery of Propranolol from a Multilaminate Adhesive Device," Pharm. Res. 6(9):753-758.
Cossum et al., 1993, "Disposition of the C-Labeled Phosphorothioate Oligonucleotide ISIS 2105 after Intravenous Administration to Rats", The Journal of Pharmacology and Experimental Therapeutics 267(3):1181-1190.
Cossum et al., 1994, "Pharmacokinetics of C-Labeled Phosphorothioate Olignucleotide, ISIS 2105 after Administration to Rats", The Journal of Pharmacology and Experimental Therapeutics, 269(1):89-94.
Crooke et al., 1994, "A Pharmacokinetic Evaluation of C-Labeled Afovirsen Sodium in Patients with Genital Warts", Clinical Pharmacology & Therapeutics 56(6):641-646.
Crowe, 1965, "Experimental comparison of intradermal and subcutaneous vaccination with influenza vaccine," Am. J. Med. Technol. 31(6):387-396.
Decision of Opposition Division Revoking EP 1296742 (Mar. 27, 2008).
Erstad et. al., 1993, "Influence of Injection Site and Route on Medication Absorption," Hospital Pharmacy 28(9), 853-854, 872-873.

Firooz et al., 1995, "Benefits and Risks of Intralesional Corticosteroid Injection in the Treatment of Dermatological Diseases", Clinical and Experimental Dermatology 20(5):363-370.
First Page of Lantus draft Product Insert submitted to the FDA (Apr. 2000).
Fjerstad, 2004, "U. Minnesota professor uses alternative flu vaccine technique," FSView & Florida Flambeau via U-Wire (Nov. 15, 2004).
Foy et al., 1970, "Efficacy of intradermally administered A2 Hong Kong vaccine," JAMA 213(1):130.
Glenn et al., 1999, "Advances in vaccine delivery: transcutaneous immunisation," Exp. Opin. Invest. Drugs 8(6):797-805.
Goodarzi et al., 1992, "Organ Distribution and Stability of Phosphorothioted Oligodeoxyribonucleotides in Mice," Biopharmaceutics & Drug Disposition 13(3):221-227.
Gramzinski et al., 1998, "Immune response to a hepatitis B DNA vaccine in Aotus monkeys: a comparison of vaccine formulation, route, and method of administration," Mol. Med. 4(2):109-118.
Halperin et al., 1979, "A comparison of the intradermal and subcutaneous routes of influenza vaccination with A/New Jersey/76 (swine flu) and A/Victoria/75: report of a study and review of the literature," Am. J. Public Health. 69(12):1247-1250.
Haynes et al., 1985,"Ultra-long-duration Local Anesthesia Produced by Injection of Lecithin-coated Methoxyflurane Microdroplets", Anestheiology 63(5):490-499.
Henry et al., 1998, "Microfabricated Microneedles: A Novel Approach to Transdermal Drug Delivery", Journal of Pharmaceutical Sciences 87(8):922-925.
Herbert et al., 1979, "Comparison of responses to influenza A/New Jersey/76-A/Victoria/75 virus vaccine administered intradermally or subcutaneously to adults with chronic respiratory disease," J. Infect. Dis. 140(2):234-238.
International Search Report mailed Apr. 21, 2006 from the International Searching Authority for PCT/US2004/014469, filed May 6, 2004.
International Search Report mailed Dec. 11, 2001 from the International Searching Authority for PCT/US2001/020763, filed Jun. 29, 2001.
International Search Report mailed Dec. 11, 2001 from the International Searching Authority for PCT/US2001/020782, filed Jun. 29, 2001.
International Search Report mailed Dec. 14, 2006 from the International Searching Authority for PCT/US2004/014033, filed May 6, 2004.
International Search Report mailed Dec. 6, 2006 from the International Searching Authority for PCT/US2005/07412, filed Mar. 8, 2005.
International Search Report mailed Oct. 6, 2003 from the International Searching Authority for PCT/US2002/040841, filed Dec. 23, 2002.
International Search Report mailed Sep. 18, 2006 from the International Searching Authority for PCT/US2005/016424, filed May 11, 2005.
International Search Report mailed Sep. 2, 2002 from the International Searching Authority for PCT/US2001/50436, filed Dec. 28, 2001.
International Search Report mailed Sep. 3, 2002 from the International Searching Authority for PCT/US2001/50440, filed Dec. 28, 2001.
International Standard ISO 9626, Stainless steel needle tubing for the manufacture of medical devices, p. 2 (Table 2—Dimensions of Tubing) of ISO 9626, 1st Edition, Sep. 1, 1991, Amendment 1, Jun. 1, 2001.
Jakobson et al., 1977, "Variations in the Blood Concentration of 1,1,2-Trichloroethane by Percutaneous Absorption and Other Routes of Administrtion in the Guinea Pig", Acta Pharmacologica et Toxicologica 41(5):497-506.
Jarratt et al., 1974, "The Effects of Intradermal Steriods on the Pituitary-Adrenal Axis and the Skin", Journal of Investigative Dermatology 62(4):463-466.
Kaushik et al., 1999, "Transdermal Protein Delivery Using Microfabricated Microneedles", 1 page.

(56) References Cited

OTHER PUBLICATIONS

Kenny et al., 2004, "Dose sparing with intradermal injection of influenza vaccine," New England Journal of Medicine 351(22):2295-2301.
Kirkpatrick et al., 1987, "Local Anesthetic Efficacy of Methoxyflurane Microdroplets in Man", Anesthesiology 67(3A):A254.
Knox et al., 2004, "New research shows intradermal rather than intramuscular vaccine injection could stretch flu vaccine supplies," National Public Radio: All Things Considered (Nov. 3, 2004).
Kohn, 2004, "Flu shot technique yields more doses, studies find; critics say injecting skin rather than muscle is too difficult for common use," The Baltimore Sun: Telegraph 3A (Nov. 4, 2004).
Leroy et al., 1984, "Pharmacokinetics of Ceftazidime in Normal and Uremic Subjects", Antimicrobal Agents and Chemotherapy 25(5):638-642.
Majeski et al., 2004, "Technique could stretch vaccine; changing the way shots are given means the current supply of flu vaccine could immunize 10 times as many people, two Minnesota physicians say" Saint Paul Pioneer Press: Main 1A (Oct. 27, 2004).
Majeski, 2004, "Alternate flu shot less effective in elderly; doctors proposed method to stretch vaccine supply," Saint Paul Pioneer Press: Main 17A (Nov. 4, 2004).
Marian et al., 2001, "Hypoglycemia activates compensatory mechanism of glucose metabolism of brain," Acta Biologica Hungarica 52(1):35-45.
McAllister et al., 1999, "Solid and Hollow Microneedles for Transdermal Protein Delivery," Proceed. Int'l. Symp. Control. Rel. Bioact. Mater. 26:192-193.
McAllister et al., 1999, "Thee-Dimensional Hollow Microneedle and Microtube Arrays," Conference: Solid-State Sensors and Actuators Transducers-Conference 12:1098-1103.
McElroy et al.. 1969, "Response to intradermal vaccination with A2, Hong Kong variant, influenza vaccine," N. Engl. J. Med. 281(19):1076.
McGugan et al., 1963, "Adrenal Suppression from Intradermal Triamcinolone", Journal of Investigative Dermatology 40:271-272.
Merriam-Webster's Collegiate Dictionary, 10th Edition, 1998, Merriam-Webster, Inc., Springfield, MA, p. 306.
Montagne et al., 2004, "Intradermal influenza vaccination—can less be more?" New England Journal of Medicine 351(22):2330-2332.
Niculescu et al., 1981, "Efficacy of an adsorbed trivalent split influenza vaccine administered by intradermal route," Arch. Roum. Path. Exp. Microbiol. 40(1):67-70.
Park, 1993, "Pharmacokinetics and Pharmacodynamics in the critically ill patient," Xenobiotica 23(11):1195-1230.
Payler, 1974, "Letter: Intradermal influenza vaccination," Br. Med. J. 2(921):727.
Payler, 1977, "Intradermal influenza vaccine using Portojet 1976," Br. Med. J. 2(6095):1152.
Pinski, 2000, p. 192 of "Soft tissue augmentation for the new millennium," Dermatological Therapy 13:192-197.
Product Brochure of Terumo Insulin Syringe (Oct. 6, 1990).
Puri et al., 2000, "An investigation of the intradermal route as an effective means of immunization for microparticulate vaccine delivery systems," Vaccine 18:2600-2612.
Rindfleisch et al., 2004, "La Crosse finding could curtail flu vaccine shortages," Wisconsin State Journal D9 (Nov. 14, 2004).
Scott et al., 1981, "Toxicity of Interferon," British Medical Journal 282:1345-1348.
Sebastien et al., 1998,"Microfabricated Needles: A Novel Approach to Transdermal Drug Delivery," Journal of Pharmaceutical Sciences 87(8):922-925.
Shute, 2004, "Second thoughts on the flu vaccine," Science & Society Public Health 137(17):80.
Smith, 2004, "Low-dose vaccine helps block flu, study says younger adults seen benefiting," The Boston Globe: National/Foreign A2 (Nov. 4, 2004).
Supersaxo et al., 1988, "Recombinant Human Interferon Alpha-2a: Delivery to Lymphoid Tissue by Selected Modes of Application," Pharmaceutical Research 5(8):472-476.
Sutherest, 1979, "Treatment of Pruritus Vulvae by Multiple Intradermal Injections of Alcohol. A Double-Blind Study," British Journal of Obstetrics and Gynecology 86:371-373.
Sveinsson, 1939, Investigation on the Influence of Insulin and Adrenalin in Rabbits with Alimentary Fatty Liver and Muscles and on the Content of Fat and Sugar in Blood:66-86.
Tauraso et al., 1969, "Effect of dosage and route of inoculation upon antigenicity of inactivated influenza virus vaccine (Hong Kong strain) in man," Bull. World Health Organ 41(3):507-516.
The American Heritage College Dictionary, 2000, 3rd Edition; Houghton Mifflin Company, Boston, New York, p. 368.
The Merck Manual of Diagnosis and Therapy (17th Ed.) 1999.
The Merck Manual of Diagnosis and Therapy, 1999, 17th Edition, Beers & Berkow, ed., Merck Research Laboratories, Division of Merck & Co., Inc., Whitehouse Station, NJ, pp. 2559-2567.
Tuft, 1931, "Active Immunization against Thyroid Fever, with Particular Reference to an Intradermal Method", Journal of Laboratory and Clinical Medicine:552-556.
Ward et al., 1975, "Pruritus Vulvae: Treatment by Multiple Intradermal Alcohol Injections," British Journal of Dermatology 93(2):201-204.
Written Opinion mailed by the International Searching Authority on Apr. 21, 2006 for PCT/US2004/014469, filed May 6, 2004.
Written Opinion mailed by the International Searching Authority on Dec. 14, 2006 for PCT/US2004/014033, filed May 6, 2004.
Written Opinion mailed by the International Searching Authority on Sep. 18, 2006 for PCT/US2005/016424, filed May 11, 2005.
Zaynoun et al., 1973, "The Effect of Intracutaneous Glucocorticoids on Plasma Cortisol Levels," British Journal of Dermatology 88(2):151-156.
Notice of Allowance mailed Dec. 11, 2013 from United States Patent and Trademark Office for U.S. Appl. No. 13/072,824.

* cited by examiner

INTRADERMAL DELIVERY OF SUBSTANCES

This application is a divisional of U.S. patent application Ser. No. 09/606,909, filed Jun. 29, 2000, which is hereby incorporated by reference in its entirety.

FIELD OF THE INVENTION

The present invention relates to methods and devices for administration of substances into the skin.

BACKGROUND OF THE INVENTION

Conventional needles have long been used to deliver drugs and other substances to humans and animals through the skin, and considerable effort has been made to achieve reproducible and efficacious delivery through the skin while reducing or eliminating the pain associated with conventional needles. Certain transdermal delivery systems eliminate needles entirely, and rely on chemical mediators or external driving forces such as iontophoretic currents or sonophoresis to breach the stratum corneum painlessly and deliver substances through the skin. However, such transdermal delivery systems are not sufficiently reproducible and give variable clinical results.

Mechanical breach of the stratum corneum is still believed to be the most reproducible method of administration of substances through the skin, and it provides the greatest degree of control and reliability. Intramuscular (IM) and subcutaneous (SC) injections are the most commonly used routes of administration. The dermis lies beneath the stratum corneum and epidermis, beginning at a depth of about 60-120 µm below the skin surface in humans, and is approximately 1-2 mm thick. However, intradermal (ID) injection is rarely used due to the difficulty of correct needle placement in the intradermal space, the difficulty of maintaining placement of the needle in the intradermal space, and a lack of information and knowledge of the pharmacokinetic profiles for many drugs delivered ID. In addition, little is known about fluid absorption limits in dermal tissue and the effect of depot time on drug stability. However, ID administration of drugs and other substances may have several advantages. The intradermal space is close to the capillary bed to allow for absorption and systemic distribution of the substance but is above the peripheral nerve net which may reduce or eliminate injection pain. In addition, there are more suitable and accessible ID injection sites available for a patient as compared to currently recommended SC administration sites (essentially limited to the abdomen and thigh).

Recent advances in needle design have reduced the pain associated with injections. Smaller gauge and sharper needles reduce tissue damage and therefore decrease the amount of inflammatory mediators released. Of particular interest in this regard are microneedles which are typically less than 0.2 mm in width and less than 2 mm in length. They are usually fabricated from silicon, plastic or metal and may be hollow for delivery or sampling of substances through a lumen (see, for example, U.S. Pat. No. 3,964,482; U.S. Pat. No. 5,250,023; U.S. Pat. No. 5,876,582; U.S. Pat. No. 5,591,139; U.S. Pat. No. 5,801,057; U.S. Pat. No. 5,928,207; WO 96/17648) or the needles may be solid (see, for example, U.S. Pat. No. 5,879,326; WO 96/37256). By selecting an appropriate needle length, the depth of penetration of the microneedle can be controlled to avoid the peripheral nerve net of the skin and reduce or eliminate the sensation of pain. The extremely small diameter of the microneedle and its sharpness also contribute to reduced sensation during the injection. Microneedles are known to mechanically orate the stratum corneum and enhance skin permeability (U.S. Pat. No. 5,003,987). However, the present inventors have found that, in the case of microneedles breaching the stratum corneum alone is not sufficient for clinically efficacious intradermal delivery of substances. That is, other factors affect the ability to deliver substances intradermally via small gauge needles in a manner which produces a clinically useful response to the substance.

U.S. Pat. No. 5,848,991 describes devices for the controlled delivery of drugs to a limited depth in the skin corresponding to about 0.3-3.0 mm and suggests that such devices are useful for delivery of a variety of drugs, including hormones. U.S. Pat. No. 5,957,895 also describes a device for the controlled delivery of drugs wherein the needle may penetrate the skin to a depth of 3 mm or less. The fluid in the pressurized reservoir of the device is gradually discharged under gas pressure through the needle over a predetermined interval, e.g., a solution of insulin delivered over 24 hrs. Neither of these patents indicates that delivery using the devices produces a clinically useful response. Kaushik, et al. have described delivery of insulin into the skin of diabetic rats via microneedles with a detectable reduction in blood glucose levels. These authors do not disclose the depth of penetration of the microneedles nor do they report any results suggesting a clinically useful glucose response using this method of administration. Further, there is no evidence of accurate or reproducible volume of delivery using such a device. WO 99/64580 suggests that substances may be delivered into skin via microneedles at clinically relevant rates. However, it fails to appreciate that clinical efficacy is dependent upon both accurate, quantitative, and reproducible delivery of a volume or mass of drug substance and the pharmacokinetic uptake and distribution of that substance from the dermal tissue.

SUMMARY OF THE INVENTION

The present invention improves the clinical utility of ID delivery of drugs and other substances to humans or animals. The methods employ small gauge needles, especially microneedles, placed in the intradermal space to deliver the substance to the intradermal space as a bolus or by infusion. It has been discovered that the placement of the needle outlet within the skin is critical for efficacious delivery of active substances via small gauge needles to prevent leakage of the substance out of the skin and to improve absorption within the intradermal space. ID infusion is a preferred method for delivery according to the invention because lower delivery pressures are required. This also reduces the amount of substance lost to the skin surface due to internal pressure which increases as fluid accumulates within the skin prior to absorption. That is, infusion minimizes effusion of the substance out of the tissue. Infusion also tends to reduce painful swelling and tissue distension and to reduce internal pressure as compared to the corresponding bolus dose. The pharmacokinetics of hormone drugs delivered according to the methods of the invention have been found to be very similar to the pharmacokinetics of conventional SC delivery of the drug, indicating that ID administration according to the methods of the invention is likely to produce a similar clinical result (i.e., similar efficacy) with the advantage of reduction or elimination of pain for the patient. Delivery device which place the needle outlet at an appropriate depth in the intradermal space and control the volume and rate of fluid delivery provide accurate delivery of the substance to the desired location without leakage.

DETAILED DESCRIPTION OF THE INVENTION

The present invention provides delivery of a drug or other substance to a human or animal subject via a device which penetrates the skin to the depth of the intradermal space. The drug or substance is administered into the intradermal space through one or more hollow needles of the device. Substances infused according to the methods of the invention have been found to exhibit pharmacokinetics similar to that observed for the same substance administered by SC injection, but the ID injection is essentially painless. The methods are particularly applicable to hormone therapy, including insulin and parathyroid hormone (PTH) administration.

The injection device used for ID administration according to the invention is not critical as long as it penetrates the skin of a subject to a depth sufficient to penetrate the intradermal space without passing through it. In most cases, the device will penetrate the skin to a depth of about 0.5-3 mm, preferably about 1-2 mm. The devices may comprise conventional injection needles, catheters or microneedles of all known types, employed singly or in multiple needle arrays. The terms "needle" and "needles" as used herein are intended to encompass all such needle-like structures. The needles are preferably of small gauge such as microneedles (i.e., smaller than about 25 gauge; typically about 27-35 gauge). The depth of needle penetration may be controlled manually by the practitioner, with or without the assistance of indicator means to indicate when the desired depth is reached. Preferably, however, the device has structural means for limiting skin penetration to the depth of the intradermal space. Such structural means may include limiting the length of the needle or catheter available for penetration so that it is no longer than the depth of the intradermal space. This is most typically accomplished by means of a widened area or "hub" associated with the shaft of the needle, or for needle arrays may take the form of a backing structure or platform to which the needles are attached (see, for example, U.S. Pat. No. 5,879, 326; WO 96/37155; WO 96/37256). Microneedles are particularly well suited for this purpose, as the length of the microneedle is easily varied during the fabrication process and microneedles are routinely produced in less than 1 mm lengths. Microneedles are also very sharp and of very small gauge (typically about 33 gauge or less) to further reduce pain and other sensation during the injection or infusion. They may be used in the invention as individual single-lumen microneedles or multiple microneedles may be assembled or fabricated in linear arrays or two-dimensional arrays to increase the rate of delivery or the amount of substance delivered in a given period of time. Microneedles may be incorporated into a variety of devices such as holders and housings which may also serve to limit the depth of penetration or into catheter sets. The devices of the invention may also incorporate reservoirs to contain the substance prior to delivery or pumps or other means for delivering the drug or other substance under pressure. Alternatively, the device housing the microneedles may be linked externally to such additional components.

It has been found that certain features of the intradermal administration protocol are essential for clinically useful pharmacokinetics and dose accuracy. First, it has been found that placement of the needle outlet within the skin significantly affects these parameters. The outlet of a smaller gauge needles with a bevel has a relatively large exposed height (the vertical "rise" of the outlet). Although the needle tip may be placed at the desired depth within the intradermal space, the large exposed height of the needle outlet allows the substance being delivered to be deposited at a much shallower depth nearer the skin surface. As a result, the substance tends to effuse out of the skin due to backpressure exerted by the skin itself and to pressure built up from accumulating fluid from the injection or infusion. For example, 200 µm microneedles are often cited as suitable means for delivery of substances through the skin. We have found, however, that even if the needle outlet is at the op of such a microneedle (without any bevel) the substance is deposited at too shallow a depth to allow the skin to seal around the needle and the substance readily effuses onto the surface of the skin. Shorter microneedles such as these serve only to permeabilize the skin and do not give sufficient dose control for utility. In contrast, microneedles according to the invention have a length sufficient to penetrate the intradermal space (the "penetration depth") and an outlet at a depth within the intradermal space (the "outlet depth") which allows the skin to seal around the needle against the backpressure which tends to force the delivered substance toward the skin surface. In general, the needle is no more than about 2 mm long, preferably about 300 µm to 2 mm long, most preferably about 500 µm to 1 mm long. The needle outlet is typically at a depth of about 250 µm to 2 mm when the needle is inserted in the skin, preferably at a depth of about 750 µm to 1.5 mm, and most preferably at a depth of about 1 mm. The exposed height of the needle outlet and the depth of the outlet within the intradermal space influence the extent of sealing by the skin around the needle. That is, at a greater depth a needle outlet with a greater exposed height will still seal efficiently whereas an outlet with the same exposed height will not seal efficiently when placed at a shallower depth within the intradermal space. Typically, the exposed height of the needle outlet will be from 0 to about 1 mm, preferably from 0 to about 300 µm. A needle outlet with an exposed height of 0 has no bevel and is at the tip of the needle. In this case, the depth of the outlet is the same as the depth of penetration of the needle. A needle outlet which is either formed by a bevel or by an opening through the side of the needle has a measurable exposed height.

Second, it has been found that the pressure of injection or infusion must be carefully controlled due to the high backpressure exerted during ID administration. Gas-pressure driven devices as are known in the prior art are prone to deviations in delivery rate. It is therefore preferable to deliver the substance by placing a constant pressure directly on the liquid interface, as this provides a more constant delivery rate which is essential to optimize absorption and to obtain the desired pharmacokinetics. Delivery rate and volume are also desirably controlled to prevent the formation of weals at the site of delivery and to prevent backpressure from pushing the needle out of the skin. The appropriate delivery rates and volumes to obtain these effects for a selected substance may be determined experimentally using only ordinary skill. That is, in general the size of the weal increases with increasing rate of delivery for infusion and increases with increasing volume for bolus injection. However, the size and number of microneedles and how closely together they are placed can be adjusted to maintain a desired delivery rate or delivery volume without adverse effects on the skin or the stability of the needle in the skin. For example, increasing the spacing between the needles of a microneedle array device or using smaller diameter needles reduces the pressure build-up from unabsorbed fluid in the skin. Such pressure causes weals and pushes the needle out of the skin. Small diameter and increased spacing between multiple needles also allows more rapid absorption at increased rates of delivery or for larger volumes. In addition, we have found that ID infusion or injection often provides higher plasma levels of drug than conventional SC administration, particularly for drugs which are susceptible to in vivo degradation or clearance. This may, in some cases, allow for smaller doses of the substance to be administered through microneedles via the ID route, further reducing concerns about blistering and backpressure.

The administration methods contemplated by the invention include both bolus and infusion delivery of drugs and other substances to human or animal subjects. A bolus dose is a single dose delivered in a single volume unit over a relatively brief time period, typically less than about 5-10 min. Infusion administration comprises administering a fluid at a selected rate (which may be constant or variable) over a relatively more extended time period, typically greater than about 5-10 min. To deliver a substance according to the invention, the needle is placed in the intradermal space and the substance is delivered through the lumen of the needle into the intradermal space where it can act locally or be absorbed by the bloodstream and distributed systemically. The needle may be connected to a reservoir containing the substance to be delivered. Delivery from the reservoir into the intradermal space may occur either passively (without application of external pressure to the substance to be delivered) or actively (with the application of pressure). Examples of preferred pressure-generating means include pumps, syringes, elastomeric membranes, osmotic pressure or Belleville springs or washers. See, for example, U.S. Pat. No. 5,957,895; U.S. Pat. No. 5,250,023; WO 96/17648; WO 96/11937; WO 99/03521. If desired, the rate of delivery of the substance may be variably controlled by the pressure-generating means. As a result, the substance enters the intradermal space and is absorbed in an amount and at a rate sufficient to produce a clinically efficacious result. By "clinically efficacious result" is meant a clinically useful biological response resulting from administration of a substance. For example, prevention or treatment of a disease or condition is a clinically efficacious result, such as clinically adequate control of blood sugar levels (insulin), clinically adequate management of hormone deficiency (PTH, Growth Hormone), expression of protective immunity (vaccines), or clinically adequate treatment of toxicity (antitoxins). As a further example, a clinically efficacious result also includes control of pain (e.g., using triptans, opioids, analgesics, anesthetics, etc.), thrombosis (e.g., using heparin, coumadin, warfarin, etc.) and control or elimination of infection (e.g., using antibiotics).

EXAMPLE 1

Figure 1:
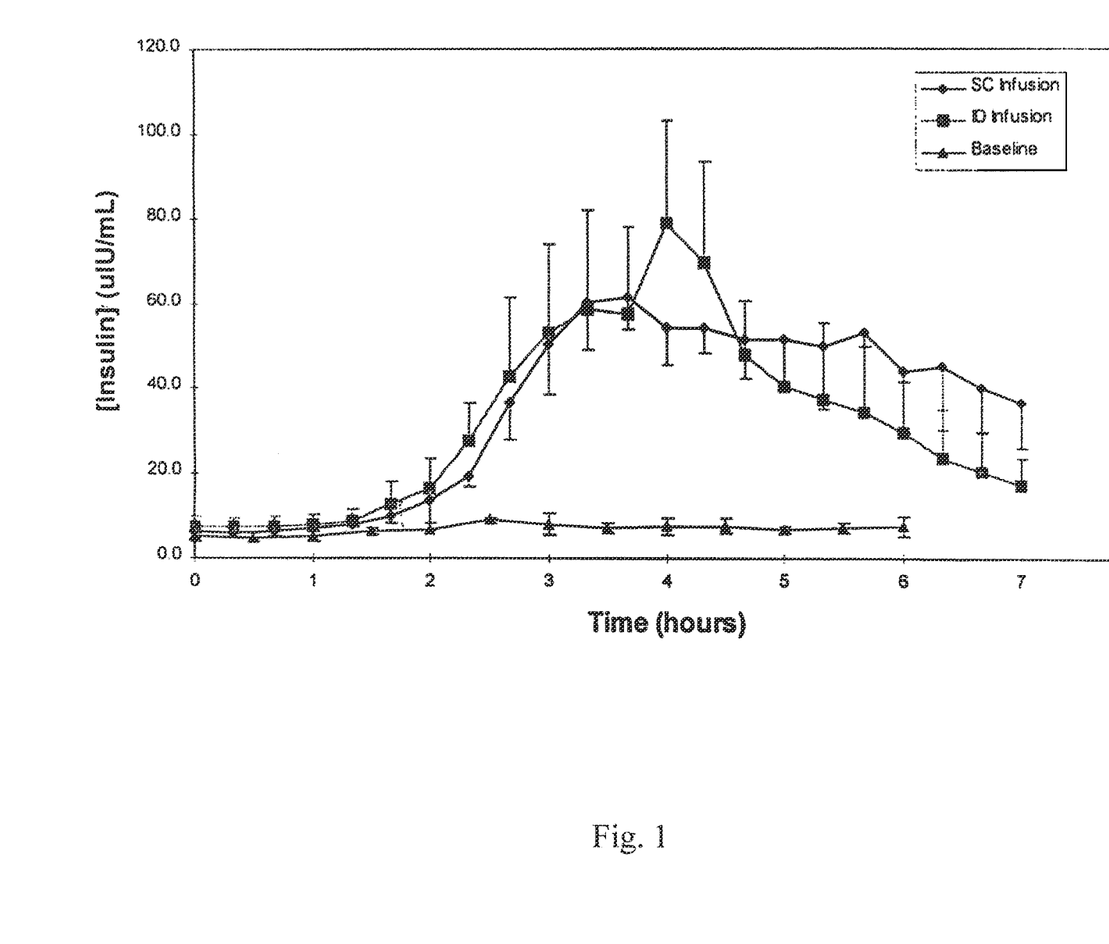
FIG. 1 illustrates the results of Example 1 for plasma insulin levels during SC and ID infusion of insulin.
Figure 2:
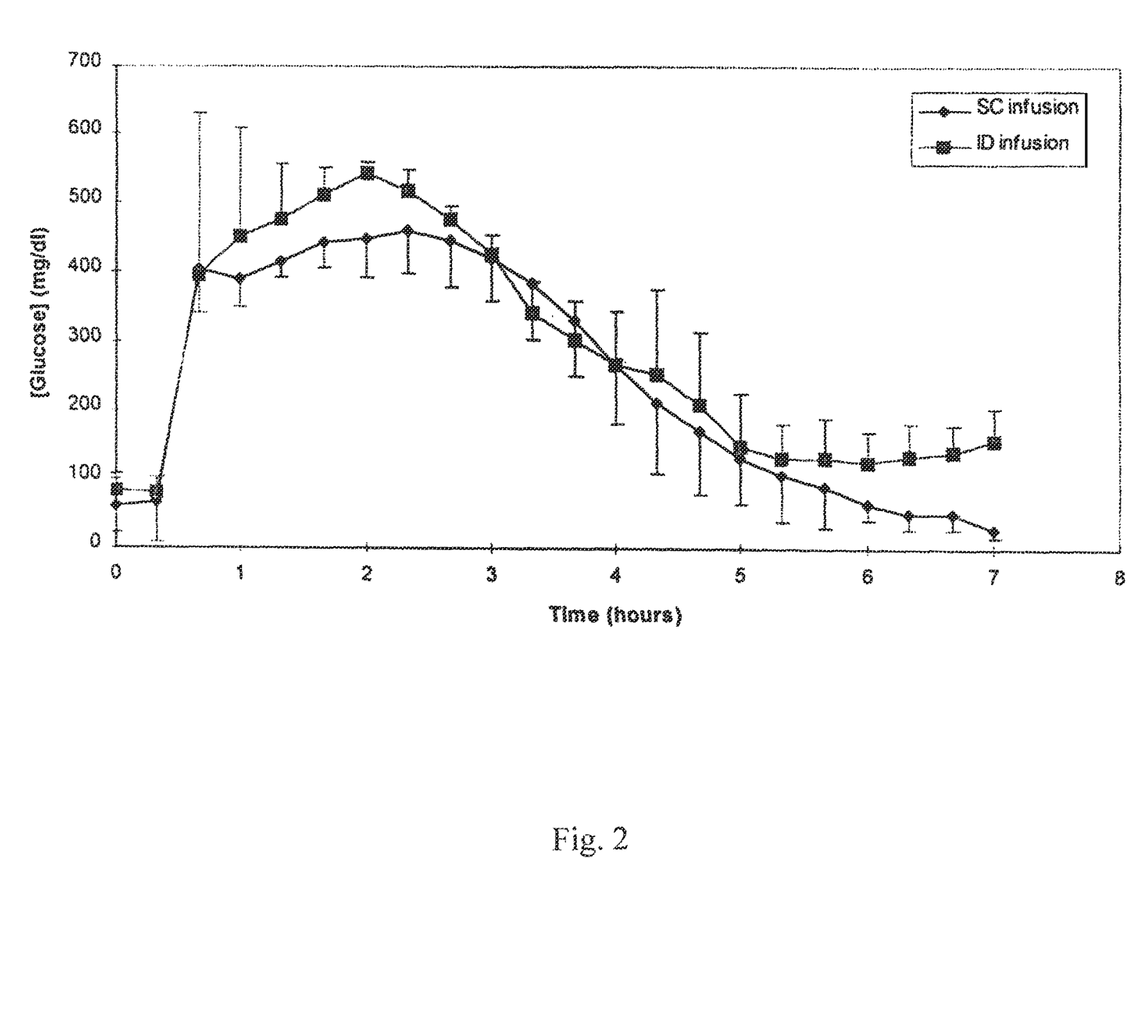
FIG. 2 illustrates the results of Example 1 for blood glucose levels during SC and D infusion of insulin.

ID infusion of insulin was demonstrated using a stainless steel 30 gauge needle bent at the tip at a 90° angle such that the available length for skin penetration was 1-2 mm. The needle outlet (the tip of the needle) was at a depth of 1.7-2.0 mm in the skin when the needle was inserted and the total exposed height of the needle outlet was 1.0-1.2 mm. The needle was constructed in a delivery device similar to that described in U.S. Pat. No. 5,957,805, with infusion pressure on the insulin reservoir provided by a plastic Belleville spring and gravimetrically measured flow rates of 9 U/hr (90 µL/hr). The corresponding flow rates for SC control infusions were set using MiniMed 507 insulin infusion pumps and Disetronic SC catheter sets. Basal insulin secretion in swine was suppressed by infusion of octreotide acetate (Sandostatin®, Sandoz Pharmaceuticals, East Hanover, N.J.), and hyperglycemia was induced by concomitant infusion of 10% glucose. After a two hour induction and baseline period insulin was infused for 2 hr. followed by a 3 hr. washout period. Plasma insulin levels were quantitated via a commercial radio-immunoassay (Coat-A-Count® insulin, Diagnostic Products Corporation, Los Angeles, Calif.), and blood glucose values were measured with a commercial monitor (Accu-chek Advantage®, Boehringer Mannheim Corp, Indianapolis, Ind.). Weight normalized plasma insulin levels and corresponding blood glucose values are shown in FIG. 1 and FIG. 2. Data indicate similar plasma insulin levels and onset periods for infusion via the ID route and via the conventional SC route. The decrease in blood glucose response is also similar between the two. Although 9 U/hr. is a higher administration rate than is typically used medically, these results also demonstrate the ability of dermal tissues to readily absorb and distribute medicaments which are infused via this pathway.

Figure 3:
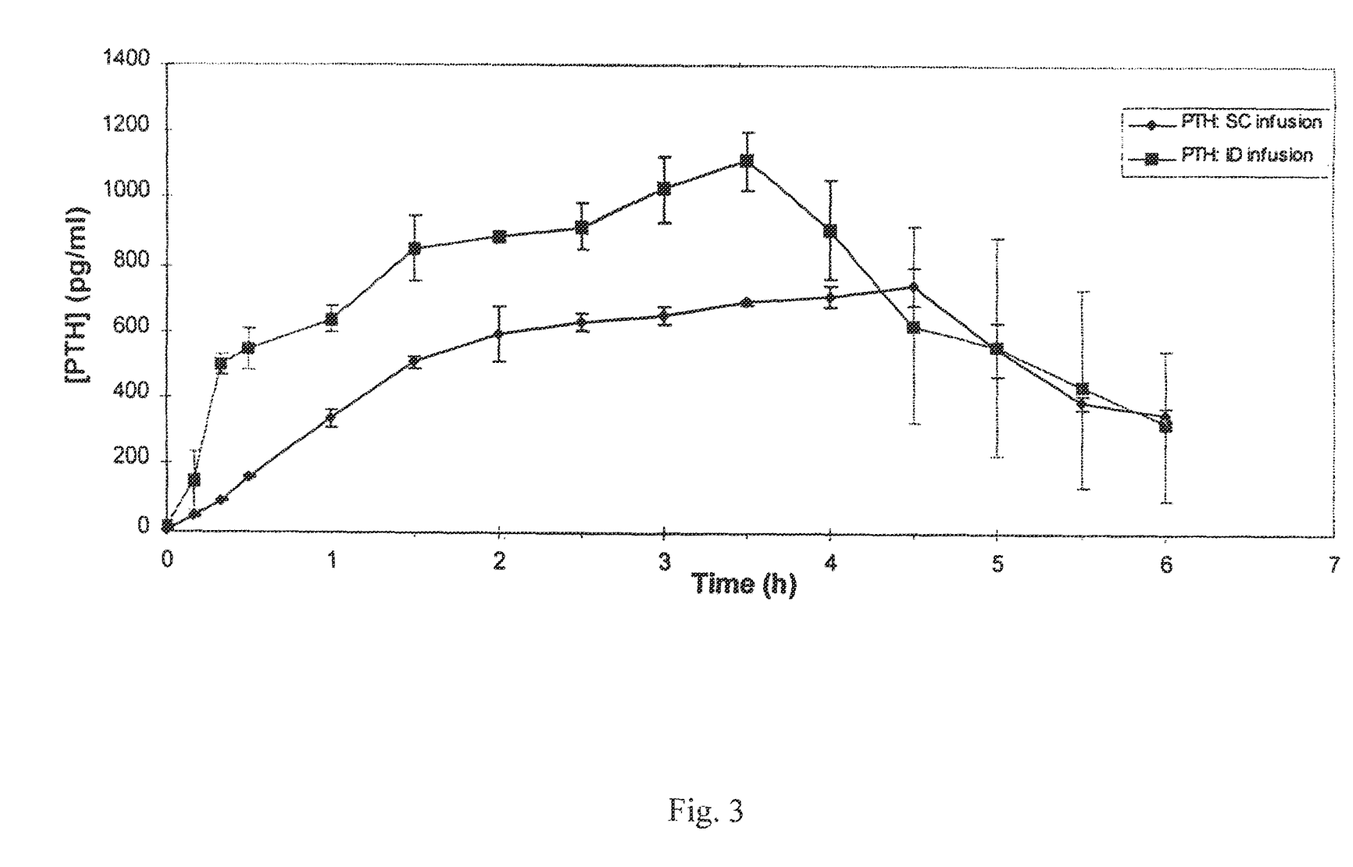
FIG. 3 illustrates the results of Example 1 for plasma PTH levels during SC and ID infusion of PTH.

A similar experiment was conducted using human parathyroid hormone 1-34 (PTH). PTH was infused for a 4 hr. period, followed by a 2 hr. clearance. Flow rates were controlled by a Harvard syringe pump. Control SC infusion was through a standard 31 gauge needle inserted into the SC space lateral to the skin using a "pinch-up" technique. ID infusion was through the bent 30 gauge needle described above. A 0.64 mg/ml. PTH solution was infused at a rate of 75 µL/hr. Weight normalized PTH plasma levels are shown in FIG. 3. This data demonstrates the efficacy of this route of administration for additional hormone drugs, and indicates that ID infusion may actually provide higher plasma levels for drugs that are susceptible to in vivo biological degradation or clearance.

EXAMPLE 2

ID insulin delivery was demonstrated in swine using a hollow microneedle connected to a standard catheter. The catheter was attached to a MiniMed 507 insulin pump for control of fluid delivery.

A hollow, single-lumen microneedle (2 mm total length and 200×100 µm OD, corresponding to about 33 gauge) with an outlet 1.0 µm from the tip (100 µm exposed height) was fabricated using processes known in the art (U.S. Pat. No. 5,929,207) and mated to a microbore catheter commonly used for insulin infusion (Disetronic). The distal end of the microneedle was placed into the plastic catheter and cemented in place with epoxy resin to form a depth-limiting hub. The needle outlet was positioned approximately 1 mm beyond the epoxy hub, thus limiting penetration of the needle outlet into the skin to approximately 1 mm, which corresponds to the depth of the intradermal space in swine. The patency of the fluid flow path was confirmed by visual observation, and no obstructions were observed at pressures generated by a standard 1 cc syringe. The catheter was connected to an external insulin infusion pump (MiniMed 507) via the integral Luer connection at the catheter outlet.

Figure 4:
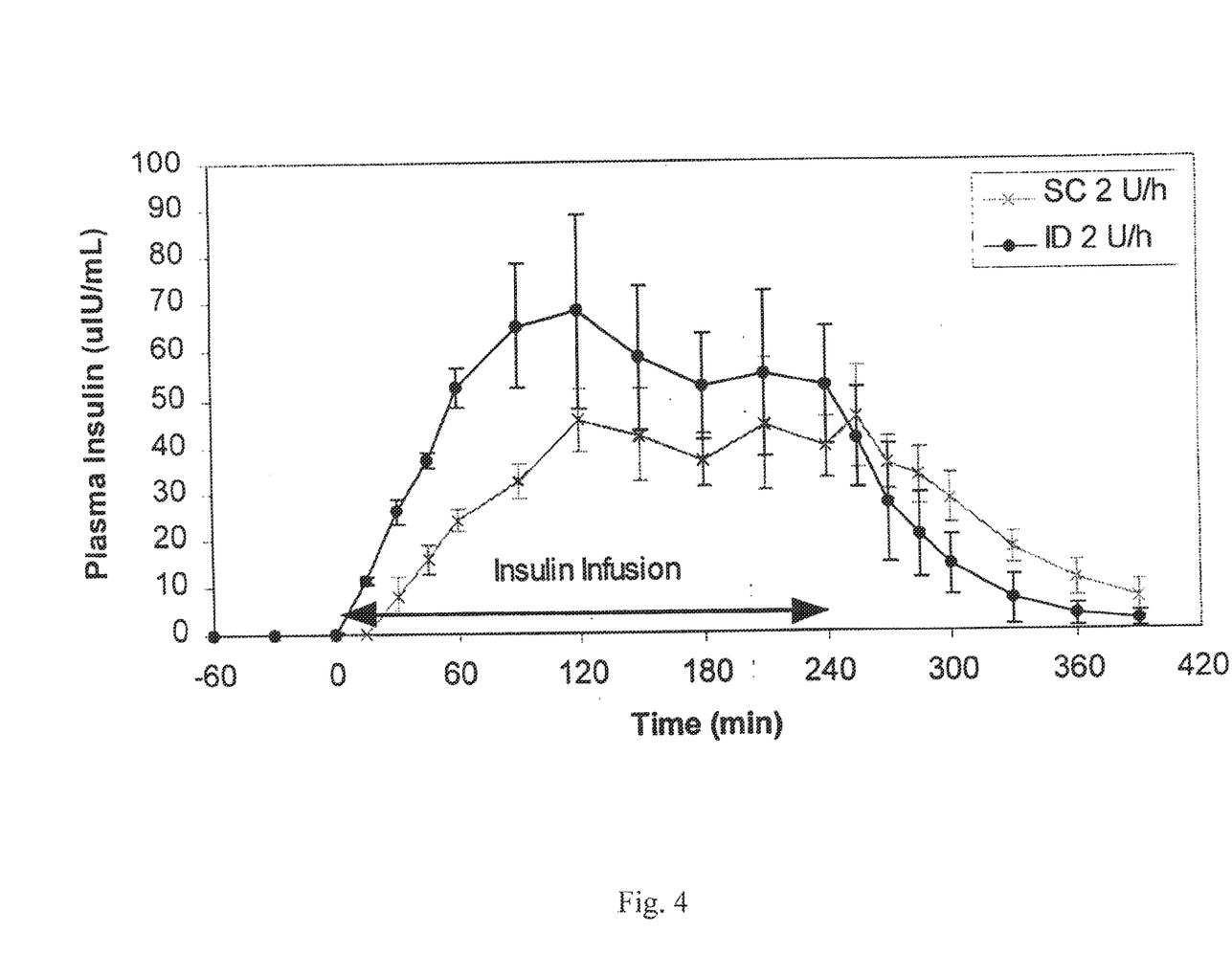
FIG. 4 illustrates the result of Example 2 for plasma insulin levels during SC and ID infusion of insulin at 2 U/hr.
Figure 5:
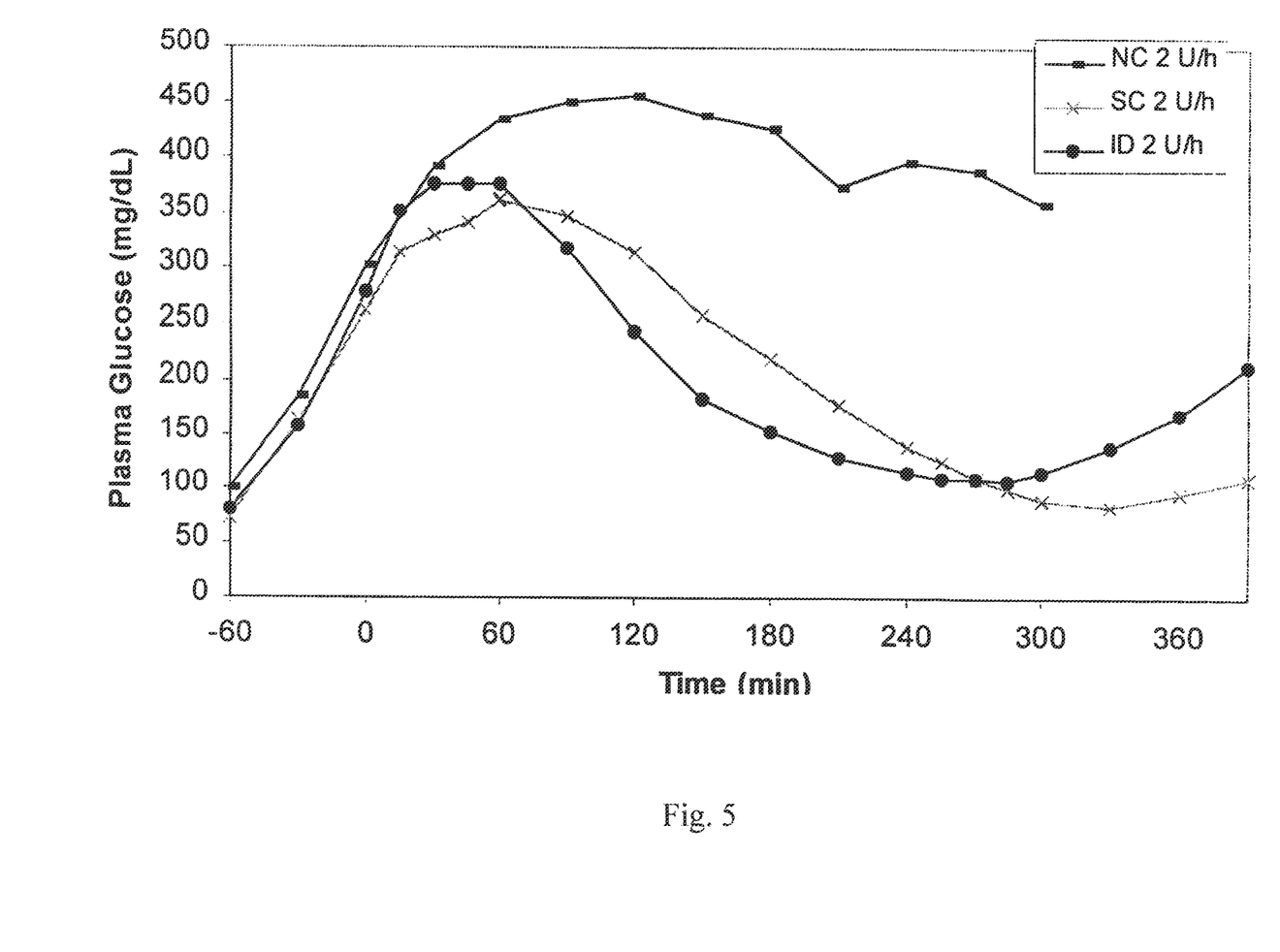
FIG. 5 illustrates the results of Example 2 for plasma glucose levels during SC and ID infusion of insulin at 2 U/hr.

The pump was filled with Humalog™ (LisPro) insulin (Lilly) and the catheter and microneedle were primed with insulin according to the manufacturer's instructions. Sandostatin® solution was administered via IV infusion to an anesthetized swine to suppress basal pancreatic function and insulin secretion. After a suitable induction period and baseline sampling, the primed microneedle was inserted perpendicular to the skin surface in the flank of the animal up to the hub stop. Insulin infusion was begun at a rate of 2 U/hr and continued for 4.5 hr. Blood samples were periodically withdrawn and analyzed for serum insulin concentration and blood glucose values using the procedures of Example 1. Baseline insulin levels before infusion were at the background detection level of the assay, as shown in FIG. 4. After initiation of the infusion, serum insulin levels showed an increase which was commensurate with the programmed infusion rates. Blood glucose levels also showed a corresponding drop relative to negative controls (NC) and this drop was similar to the drop observed for conventional SC infusion (FIG. 5).

In this experiment, the microneedle was demonstrated to adequately breach the skin barrier and deliver a drug in vivo at pharmaceutically relevant rates. The ID infusion of insulin was demonstrated to be a pharmacokinetically acceptable administration route, and the pharmacodynamic response of blood glucose reduction was also demonstrated. This data indicates a strong probability of successful pharmacological results for ID administration of hormones and other drugs in humans according to the methods of the invention.

What is claimed is:

1. A method for administration of insulin to a human subject, comprising delivering the insulin through the lumen of a hollow needle into an intradermal compartment of the human subject's skin, which method comprises;
   (a) inserting the needle into the subject's skin so that the needle penetrates the intradermal compartment, and the needle's outlet depth and exposed height of the outlet are located within the intradermal compartment, wherein the outlet has an exposed height of about 0 to 1 mm; and
   (b) delivering the insulin through the lumen of the needle with the application of pressure in an amount effective to control the rate of delivery of the insulin,
so that the insulin is delivered through the lumen of the needle into the intradermal compartment and distributed systemically exhibiting a faster onset of a detectable plasma level and a higher maximum plasma concentration as compared to subcutaneous delivery.

2. The method of claim 1, wherein the needle is selected from the group consisting of microneedles, catheter needles, and injection needles.

3. The method of claim 1, wherein a single needle is inserted.

4. The method of claim 1, wherein multiple needles are inserted.

5. The method of claim 1, wherein the needle is about 300 µm to 2 mm long.

6. The method of claim 1, wherein the needle is about 500 µm to 1 mm long.

7. The method of claim 1, wherein the outlet is at a depth of about 250 µm to 2 mm when the needle is inserted.

8. The method of claim 1, wherein the outlet is at a depth of about 750 µm to 1.5 mm when the needle is inserted.

9. The method of claim 1, wherein the outlet has an exposed height of about 0 to 300 µm.

10. The method of claim 1, wherein the delivery rate or volume is controlled by spacing of multiple needles, needle diameter or number of needles.

* * * * *